(12) United States Patent
Attie et al.

(10) Patent No.: US 7,517,860 B1
(45) Date of Patent: Apr. 14, 2009

(54) INHIBITION OF LIPOPROTEIN SECRETION

(75) Inventors: Alan D Attie, Madison, WI (US);
Donald L Gillian-Daniel, Madison, WI (US); Paul W. Bates, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/620,820

(22) Filed: Jul. 21, 2000

(51) Int. Cl.
*A61K 48/00* (2006.01)
*C12N 15/63* (2006.01)

(52) U.S. Cl. .................. 514/44; 435/320.1; 435/455
(58) Field of Classification Search .................. 514/44; 435/320.1; 536/23.1, 24.1
See application file for complete search history.

(56) References Cited

U.S. PATENT DOCUMENTS 5,521,071 A 5/1996 Attie et al.

OTHER PUBLICATIONS

Conner et al., Abstracts from scientific sessions 2000, 2000, Supplement to Circulation, vol. 102, pp. 720.*
Teasdale et al., Signal-mediated sorting of membrane proteins between the endoplasmic reticulum and the golgi apparatus, 1996, Annu. Rev. Cell. Dev. Biol. vol. 12, pp. 27-54.*
Verma et al. Gene therapy-promises, problems and prospects. 1997, Nature, vol. 389, pp. 239-242.*
Anderson et al. Human gene therapy. 1988, Nature, vol. 392, pp. 25-30.*
Palu et al. In pursuit of new developments for gene therapy of human diseases. 1999, Journal of Biotechnology, vol. 68, pp. 1-13.*
Chiba et al. Journal of Biological Chemistry, 1998. vol. 273, No. 41, pp. 26298-26304.*
Rick Weiss, FDA Halts Gene Therapy Experiments. Washington Post, Mar. 3, 2005.*
Gotthardt and Schuster, Gene therapy for familial hypercholesterolmia. Concepts in Gene Therapy, 1997, p. 359-386.*
Twisk, et al., "The role of the LDL receptor in apolipoprotein B secretion," *The Journal of Clinical Investigation* 105:4:521-532 (plus 2 pages Supplement) (2000).
Braun, A., et al., "Loss of SR-BI Expression leads to the Early Onset of Occlusive Atherosclerotic Coronary Artery Disease . . . ," Cir. Res. 90:270-276 (2002).
Breslow, J.L. et al., "Transgenic Mouse Models of Lipoprotein Metabolism and Athersclerosis," Proc. Natl. Acad. Sci. USA 90:8314-8318 (1993).
Clee, S.M., et al., "The Genetic Landscape of type 2 Diabetes in Mice," Endocrine Reviews 28:48-83 (2007).
De Winther, M.P.J., et al, "New mouse models for lipoprotein metabolism and atherosclerosis," Current Opinion in Lipidology 13:191-197 (2002).
Grass, D.S., et al, "Transgenic mice expressing both human apolipoprotein B and human CETP . . . ," Journal of lipid Research 36:1082-1091 (1995).

Herrera, V.L.M., et al., "Spontaneous combined hyperlipidermia, coronary heart disease and decreased survival . . . ," Nature medicine 5:1383-1389 (1999).
Marschang, P., et al., "Mouse models as tools for dissecting disorders of lipoprotein metabolism," Cell & Developmental Biology 14:25-35 (2003).
Masucci-Magoulas, L., et al., "A mouse model with features of familial combined hyperlipidermia," Science 275:391-394 (1997).
Melman, A., et al., "hMaxi-K Gene Transfer in Males with Erectile Dysfunction: Results of the First Human Trial," Human Gene Therapy 18:1165-1176 (2006).
Sharpless, N.E., et al., "The mighty mouse: genetically engineered mouse models in cancer drug development," Nature Rev. Drug Discovery 5:741-754 (2006).
Takahashi, H., et al., "Effect of CETP on the Plasma Lipoprotein Profile in Four Strains of Transgenic Mouse," Biochemical and Biophysical Res. Com. 283:118-123 (2001).
Zhang, S., et al., "Diet-Induced occlusive Coronary Atherosclerosis, Myocardial Infarction . . . ," Circulation 111:3457-3464 (2005).
Kahle, P.J., et al., "The emerging utility of animal models of chromic neurodegenerative diseases," Emerging Therapeutic Targets5:125-132 (2001).
Warrington K.H., Jr., et al., "Treatment of human disease by adeno-associated viral gene transfer," Hum Genet 119:571-603 (2006).
Anderson, W. F., "The Best of Times, the Worst of Times," Science 288:627-629 (2000).
Cavazzana-Calvo, M., et al., "Gene Therapy of Human Severe Combined Immunodeficiency (SCID)-X1 Disease," Science 288:669-672 (2000).
Kay, M. A., et al., "Evidence for gene transfer and expression of factor IX in haemophila B patients treated with an AAV vector," Nature Genetics 24:257-261 (2000).
Agnello, V., et al., "Hepatitis C virus and other Flaviviridae viruses enter cells via low density lipoprotein receptor," PNAS 96:12766-12771 (1999).
Davis, C.G., et al., "Acid-dependent ligand dissociation and recycling of LDL receptor mediated by growth factor homology region," Nature 326:760-765 (1987).
Krey, T. et al., "Role of the Low-Density Lipoprotein Receptor in Entry of Bovine Viral Diarrhea Virus," Journal of Virology 80:10862-10867 (2006).
Petit, J-M., et al., "Cell surface expression of LDL receptor in chronic hepatitis C: correlation with viral load," Am. J. Physiol. Endocrinol. Metab. 293:E416-E420 (2007).
Rudenko, G., et al., "Structure of the LDL Receptor Extracellular Domain at Endosomal pH," Science 298:2353-2358 (2002).

* cited by examiner

*Primary Examiner*—Celine X Qian
(74) *Attorney, Agent, or Firm*—Quarles & Brady LLP

(57) ABSTRACT

It has been discovered that the low density lipoprotein receptor (LDLR) degrades the lipoprotein apoB. Based on this observation, an artificial fusion protein has been designed containing an LDL receptor domain attached to a localization domain which causes retention of the fusion protein inside of a cell. The fusion protein is preferably retained in the endoplasmic reticulum of the cell, where the LDLR can degrade apoB. Data shows that the technique is effective in a mammal to reduce serum LDL cholesterol levels.

12 Claims, 2 Drawing Sheets

INHIBITION OF LIPOPROTEIN SECRETION

STATEMENT REGARDING FEDERALLY SPONSORED RESEARCH OR DEVELOPMENT

The invention was made with United States government support awarded by the following agencies:
NIH HL56593
The United States has certain rights in this invention.

CROSS-REFERENCE TO RELATED APPLICATIONS

Not applicable.

BACKGROUND OF THE INVENTION

Approximately two-thirds of plasma cholesterol in humans is transported on low-density lipoprotein (LDL) molecules. The concentration of LDL in the bloodstream is strongly correlated with the risk of developing premature heart disease to the extent that drugs are designed to lower serum LDL levels. Drugs that reduce the level of LDL in the bloodstream have been shown in numerous clinical trials to be effective in reducing the risk of developing heart disease. The most notable examples are the "statins" (e.g. Zocor, Simvastatin, Lovastatin, Atorvastatin, Pravastatin), drugs that inhibit the activity of 3-hydroxy-3-methyl-glutaryl-coenzymeA reductase, an enzyme in the cholesterol biosynthetic pathway. However, people vary in their responsiveness to these drugs. In particular, some patients with severe forms of hypercholesterolemia are not very responsive to statins or to any other known drug therapy.

An elevation in serum LDL levels can be caused by diminished clearance of LDL particles from the circulation or by increased production of LDL or both. The clearance of LDL from the circulation is largely mediated by the LDL receptor. Thus, patients with familial hypercholesterolemia, a disease caused by LDL receptor mutations, have LDL levels 8-10-fold elevated (in the homozygous form) or 2-4-fold elevated (in the heterozygous form), as compared to patients with normal LDL receptor. This observation provides strong support for the key role of the LDL receptor in LDL metabolism.

LDL particles are not directly synthesized. Rather, the liver produces very low density lipoprotein (VLDL), which is secreted into the bloodstream. While the bloodstream, VLDL is converted into LDL. This occurs through the action of lipoprotein lipase (LPL), an enzyme residing on the lumenal surface of the capillary endothelium. LPL catalyzes the hydrolysis of the triglycerides in the VLDL particle, thus shrinking the diameter of the particle and enriching it for cholesterol and cholesterol ester (cholesterol ester is not a substrate for LPL). VLDL also acquires cholesterol ester through the action of cholesterol ester transfer protein (CETP). CETP is in the bloodstream and promotes the transfer of cholesterol ester from HDL to VLDL and the reciprocal transfer of triglyceride from VLDL to HDL. Thus, the actions of LPL and CETP lead to the conversion of a triglyceride-rich particle, VLDL, to a cholesterol-rich particle, LDL.

Excessive secretion of VLDL can lead to high levels of plasma VLDL and/or high levels of plasma LDL. Overproduction of VLDL has been seen as a metabolic consequence of many mutations in the LDL receptor. In addition, a separate metabolic disorder, termed "familial combined hyperlipidemia", also involves the overproduction of VLDL. Consequently, another strategy for dealing with disorders resulting in excessive VLDL (hypertriglyceridemia), excessive LDL (hypercholesterolemia), or both (combined hyperlipidemia) is to interfere with the production and/or secretion of VLDL.

BRIEF SUMMARY OF THE INVENTION

The present invention is, in one aspect, summarized in that a genetic construct includes a promoter operably linked to a protein coding sequence, the protein coding sequence coding for the expression of a fusion protein. The fusion protein includes a low density lipoprotein receptor and a localization domain that acts as a signal for the transport of the protein to the interior of a cell.

The present invention is also summarized in a method which begins with the step of making a genetic construct which includes a protein coding sequence encoding for the expression of a fusion protein. The fusion protein includes a low density lipoprotein receptor and a localization domain which directs localization of the fusion protein to the interior of a cell in the individual. The construct also includes a promoter effective in the cells of the individual to express the protein coding sequence. The subsequent step is to deliver the genetic construct into the individual.

It is an object of the present invention to provide a methodology to lower serum LDL levels in individuals.

It is another object of the present invention to provide a method to reduce plasma triglycerides in individuals.

Other objects, advantages and features of the present invention will become apparent from the following specification.

DETAILED DESCRIPTION OF THE INVENTION

Figure 1:
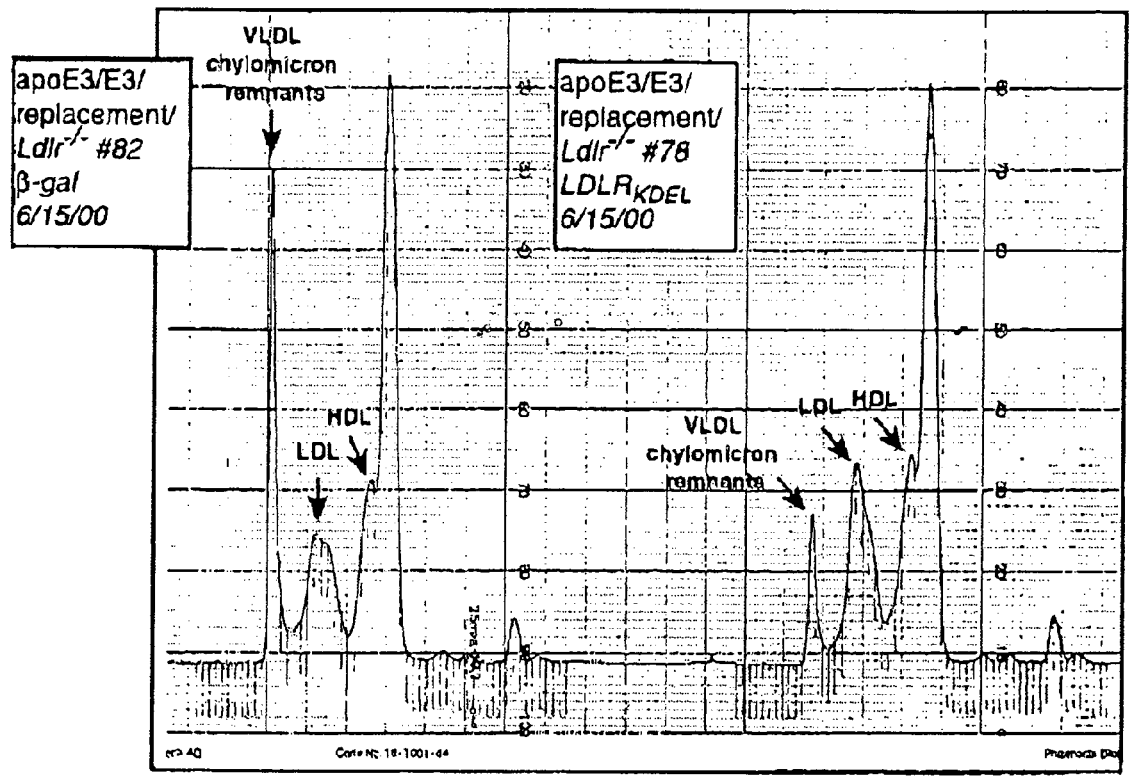
FIG. 1 is a graphical illustration of some of the data from the examples below.

The present invention is based, in part, upon the observation that the functioning of the low density lipoprotein receptor (LDLR) is directly linked to secretion of apolipoprotein B (apoB), the core protein component of VLDL, and hence of LDL. Since LDLR regulates apoB secretion, by facilitating degradation of apoB, it then becomes possible to consider methodologies to use engineered derivatives of native LDLR to inhibit secretion of apoB and thus act to lower serum LDL levels. This same strategy should also result in reduced plasma triglycerides in the treated individuals. It is believed that the LDL receptor and apoB interact early in the secretory pathway, likely in the endoplasmic reticulum (ER) and that degradation of apoB is a result of that interaction. This understanding lead to the design of LDLR constructs intended to be retained inside of the cell, rather than exported to the exterior cell surface, to which native LDLR is normally transported. A derivative of LDLR capable of accomplishing this objective is a truncated form of the LDLR protein to which is appended a sequence capable of localizing the derivative protein in the ER. A truncated form of the LDLR protein, still capable of performing the LDL binding function, but lacking the membrane anchoring region of the native protein, is described in U.S. Pat. No. 5,521,071. That truncated form of the LDLR includes the repeat sequences at the amino terminus of the protein which provide the LDL binding function but does not include the domain associated with membrane binding or the domain associated with O-linked sugars. The truncated LDLR has been shown to be expressed in a conformationally correct form for LDL binding. To that truncated LDLR protein, a localization domain is added. The localization domain is intended not to transport the fusion protein to the cell surface, but to retain the fusion protein inside of the cell. This domain may be as simple as a four amino acid sequence, such as KDEL or HDEL. These tetrapeptides actuate localization of the protein to which they are attached to the ER.

Thus it is envisioned here that gene expression constructs be made which code for the expression of a fusion protein of two parts. One part is a truncated LDLR domain which is truncated so that it is not passed to the extracellular surface but which can effectively bind to LDL. The second part of the fusion protein is a localization domain which is intended to localize the fusion protein inside of the cell producing it. The idea here is that the LDLR is localized inside of the cells, preferably in the ER, where the LDLR will facilitate degradation of apoB. Thus the localization domain that is preferable is one that directs the localization of the fusion protein to an intracellular membrane. Described here are several alternatives for localization domains which will direct the localization of the fusion protein to the ER.

One set of alternatives for the localization domain includes the variants on the Lys-Asp-Glu-Leu (KDEL) amino acid sequence. Proteins tagged with one of these signals are selectively retrieved from a post-ER compartment by a receptor and returned to their normal location. While the KDEL signal is preferred, the following variants are known to be effective in various hosts:

| Signal | Species |
|---|---|
| KDEL, KEEL | Vertebrates, *Drosophila, C. elegans,* plants |
| HDEL | *Saccharomyces. cerevisiae, Kluyveromyces lactis,* plants |
| DDEL, QDEL | *Kluyveromyces lactis* |
| ADEL | *Schizosaccharomyces pombe* (fission yeast) |
| SDEL | *Plasmodium falciparum* |

Other possible alternatives for intracellular localization signal domains include any cytoplasmic, lumenal (e.g. R402Q variant of human tyrosinase) and transmembrane domains (e.g. CYP2C1) or signals which contain independent ER localization signals such as ribophorin II. Another strategy is to make mutations by amino acid substitution deletion or addition in cytoplasmic, lumenal or transmembrane domains which result in localization in the ER. Some proteins can be retained in the ER if they have impaired or inhibited glycosylation, as from improper folding, such as Kex2p and sialyltransferase II, and that technique could be used to make a localization domain. Sometimes the inhibition of glycosylation can permit interactions with chaperones resulting in cellular retention of proteins as well. Chaperone protein overproduction can also inhibit protein secretion.

The localization domain is produced with the LDLR in such a manner as to maintain the LDLR binding of apoB while permitting the intended localization. The preferred methodology is to locate the localization domain at the carboxyl end of the fusion protein, but amino terminal fusions may work in some instances.

It is envisioned the DNA constructs encoding a fusion protein as described here can be effectively introduced into any mammal to result in lowered levels of apoB. The mechanism described here to facilitate the degradation of apoB is one that operates at a cellular level, and the relevant cellular mechanisms are similar in mammals. For humans, mice are a recognized animal model for testing of LDL lowering strategies.

It is envisioned that a DNA construct encoding the fusion protein of the present invention can be inserted into any expression vector that can cause expression of an inserted protein coding sequence in the host of choice. Such expression construct are transfected into cells which are then altered so as to decrease apoB production. The result is achieved whether or not the cells are treated in vitro or in vivo, provided only that an expression system appropriate for the host is chosen. As the data below demonstrates, it is possible to introduce an expression construct for the LDLR/localization domain fusion protein into an individual in vivo with the result that meaningful decreases in apoB levels are observed. Thus treatment of individuals, as well as cells, is contemplated.

EXAMPLES

In vitro Experiments

Vector. The DNA sequence encoding the soluble truncated LDL receptor was obtained from a vector as described in U.S. Pat. No. 5,521,071, which encodes a 354 amino acid LRLR. The protein coding sequence was excised from a plasmid pAcLDLR3m, which is described in Dirlam et al., *Protein Expr. Purif.* 8(4):489-500 (1996), using the restriction enzyme Bam HI. The fragment was then inserted into the plasmid pAdBM5 (Quantum Biotechnologies, Inc., Quebec, Canada). The amino acid sequence gln-lys-ala-val-lys-asp-leu-stop (QKAVKDELstop) was introduced into the plasmid beginning at nucleotide position 5257 (amino acid 355) in the $LDLR_{354}$ coding sequence. To do this, two complementary oligonucleotides consisting of the desired sequence were annealed together and ligated into a unique Bgl II site in the plasmid. The sequences encoding the $LDLR_{354}$ and $LDLR_{KDEL}$ were then cloned into the plasmid pAdTRACKCMV, as described in He et al., *Proc. Natl. Acad. Sci. USA* 95(5): 2509-14 (1998). This plasmid then contained a cytomegalovirus (CMV) promoter upstream from the $LDLR_{KDEL}$ sequence allowing for efficient protein expression in mouse lymphocytes. This plasmid was used for both the in vitro and in vivo studies described below.

Preparation of mouse hepatocytes. Hepatocytes were isolated by liver perfusion and seeded at subconfluency in Dulbecco's Modified Eagle Medium (DMEM; GIBCO-BRL supplemented with fetal bovine serum (FBS; 10% v/v; Hyclone), insulin (20 mU/ml; Novo Nordisk) and dexamethasone (25 nM; Sigma). Cells were left to attach for 4 hours in an incubator at 37° C. with 5% $CO_2$. Following a wash with DMEM, the cells were cultured overnight in DMEM supplemented with 10% FBS and 20 mU/ml insulin. On the following day, cells were transfected with an expression pAdTRACKCMV-$LDLR_{KDEL}$ for a fusion protein of the LDLR truncated receptor with the KDEL localization domain, or $LDLR_{KDEL}$, or with a control plasmid. The transfections were performed using the TransIT-Insecta transfection reagent (Mirus) following the manufacturer's protocol, except that the transfections were performed using 10 μg DNA and 40 μl TranIT-Insecta reagent per 2 ml supplemented with DMEM and 10% FBS in a 60 mm dish of cultured heptocytes. Transfected hepatocytes were cultured for an additional 36-48 hour period prior to further experimentation.

Labeling. The hepatocytes were incubated for 1 hour in starve medium before pulse-labeling for 7.5 minutes with radioactive tracer (200 μCi [$^{35}$S] methionine/cysteine/60 mm dish). The dishes were washed one time with DMEM prior to addition of chase medium (DMEM supplemented with 10 mM each of labeled methionine and cysteine and 0.2 mM oleic acid).

Immunoprecipitation. Following the radiolabeling, the media were collected and centrifuged (5 min., 1000 rpm). The resulting media were used for immunoprecipitations. Cells were rinsed three times with ice-cold PBS, scraped into PBS, and collected by centrifugation. The cell pellets were lysed in 200 μl RIPA/1% SDS (150 mM NaCl; 50 mM Tris (pH 7.5); 1% Triton X-100; 0.5% deoxycholate; 1% SDS; 1 mM PMSF; 1 mM orthovanadate; 10 μg/ml trypsin inhibitor; 10 μg/ml leupeptin). The mixture was then diluted five times to 1 ml final volume in 150 mM NaCl; 50 mM Tris (pH 7.4); 1 mM PMSF; 1 mM orthovanadate; 10 mg/ml trypsin inhibitor; 10 mg/ml leupeptin. For immunoprecipitations, both the media and the cell lysates were supplemented with 1/5 volume IMB (100 mM Tris (pH 7.4), 25 mM EDTA, 5 mg/ml BSA; 2.5% sodium deoxycholate, 2.5% Triton X-100, 0.01% sodium azide). Antibodies to apoB (polyclonal, rabbit anti-pig LDL) or albumin (polyclonal, rabbit anti-human serum albumin; Sigma) were also added. For the precipitations of albumin, IMB did not contain BSA. After an overnight incubations at 4° C., Protein A-agarose beads (Gibco-BRL) were added and the incubation continued at 4° C. overnight. The antibody/bead slurry was subsequently washed, once with PBB (10 mM phosphate buffer (pH 7.4), 1 mg/ml BSA, 0.01% sodium azide) and once with PB (PBB without BSA). Radiolabeled protein was solubilized in SDS-sample buffer (2% SDS, 20% glycerol, 50 mM Tris (pH 6.8), 6 M urea, 1 mM EDTA, 20 mg/ml bromophenol blue), supplemented with 10 mM DTT and 250 mM β-mercaptoethanol, and heated at 65° C. for 30 minutes prior to SDS polyacrylamide gel electrophoresis (SDS-PAGE). Specific proteins were visualized by autoradiography and the amounts on unlabeled protein were determined by storage phosphor technology (PhosphorImager, Molecular Dynamics; ImageQuant version 3.3). All data was normalized to cellular protein and total TCA-precipitable radiation.

Results. The expression of the $LDLR_{KDEL}$ construct in primary hepatocytes resulted in a decrease in the secretion of apoB100-containing lipoproteins. The decrease in apoB100 levels was greater than 50%. Levels of apoB48 were reduced but less than 50%. This reduction was correlated with the expression of the $LDLR_{KDEL}$ protein. The reduction was not observed in the cells transformed with the control plasmid expressing b-galactosidase. Transfection efficiencies ranged between 40 and 60%, suggesting that the reduction of apoB reported here is underestimated. Intracellular levels for triglycerides did not vary between the experimental and control cells.

In vivo Experiments

In a first trial, plasmids encoding either $LDLR_{KDEL}$ or β-galactosidase (control) were injected into a tail vein of mice lacking a functional LDL receptor. Approximately 48 hours after the injection, the mice were fasted for 4 hours and then sacrificed. Plasma from the mice was harvested, diluted 1:1 with PBS, filtered and fractionated using a Pharmacia Sepharose 6 column. The protein profile from that analysis is illustrated in FIG. 1. In FIG. 1, the VLDL/chylomicron remnant, LDL and HDL peaks are identified. Traces are representative for three animals for the control and two for the experimentals. The third experimental animal exhibited no change. Strikingly, the animal with the highest $LDLR_{KDEL}$ expression level, as determined by Western blot analysis, showed an about 50% reduction in plasma cholesterol levels (245.8 mg/dl before injection and 124.6 mg/dl after). Cholesterol levels showed little or no change in plasma from control animals.

Figure 2:
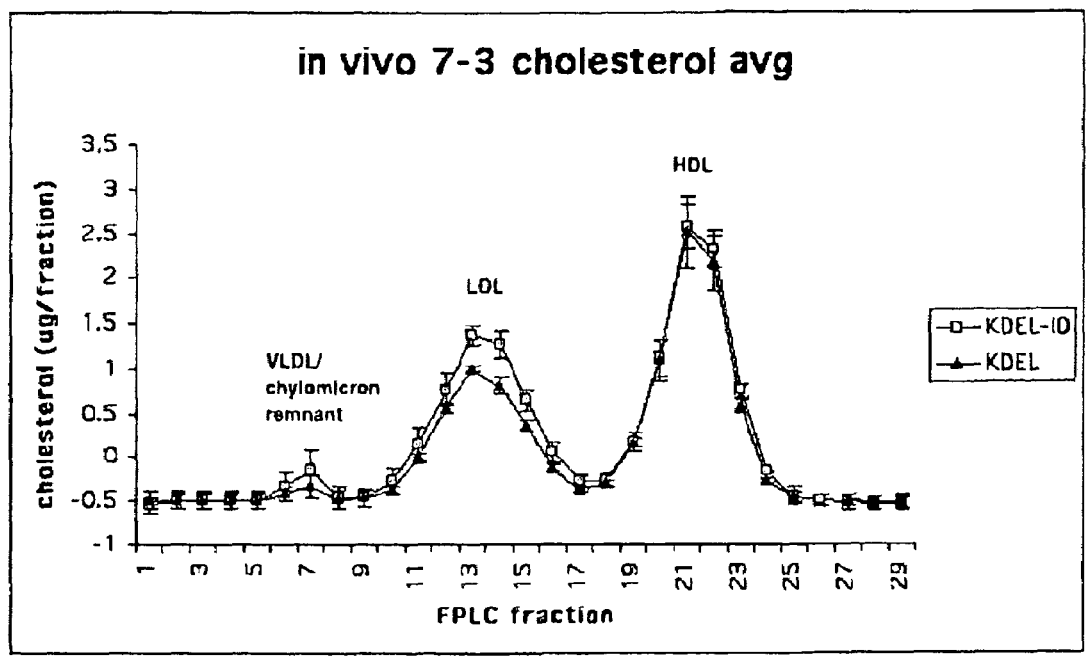
FIG. 2 is a graphical representation of more of the data from the examples below.

The second trial using the $LDLR_{KDEL}$ vector in vivo was performed in mice which possessed a wild-type LDL receptor. In this trial the control selected was a plasmid encoding a protein that differs from the KDEL motif by a single amino acid substitution (Ile (140) to Asp). This variant, designated KDEL-ID, was predicted to be deficient in apoB binding and appeared from in vitro experimentation to be a suitable control. Mice were injected in a tail vein with 25 μg of DNA coding for either $LDLR_{KDEL}$ or the KDEL-ID variant. Experiments were performed using the Trans-IT In Vivo protocol (Mirus Corporation) according to the manufacturer's instructions. Plasma was harvested approximately 48 hours after injection following a 4 hour fast. The recovered plasma was diluted 1:1 with PBS, filtered and lipoprotein particles were separated on a Sepharose 6 gel filtration FPLC column (Pharmacia). Cholesterol values for each fraction were determined enzymatically (Sigma). The data is shown in FIG. 2, which represents the mean values for three animals for each treatment, the error bars representing standard error of the mean. The VLDL/chylomicron remnant, LDL and HDL peaks are indicated. This data demonstrates a reproducible lowering of cholesterol levels by about 20%. This result is striking due to the quite low initial VLDL/LDL cholesterol levels in these mice. Additionally, these results may be understated. A mouse HDL particle (HDL-1) co-migrated with LDL and thus may partially mask the effect from the $LDL_{KDEL}$ treatment.

We claim:

1. A method for the lowering of serum cholesterol levels in a mammal comprising the steps of
preparing a nucleic acid construct comprising a DNA sequence encoding a fusion protein, operably linked to a promoter for expression in a cell, wherein the fusion protein comprises (a) a truncated soluble low density lipoprotein receptor, which includes the functional low density lipoprotein binding domain, but does not include the membrane binding domain or the domain associated with O-linked sugars, and (b) a localization domain signal peptide, which retains the fusion protein in the endoplasmic reticulum of a cell; and
administering the nucleic acid construct systematically to the mammal, wherein expression and production of said fusion protein results in the lowering of serum cholesterol levels in said mammal.

2. The method as claimed in claim 1, wherein the low density lipoprotein receptor is LDL-$R^{354}$.

3. The method as claimed in claim 1, wherein the localization domain is selected from the group consisting of the amino acid sequences KDEL, KEEL, HDEL, DDEL, QDEL, ADEL and SDEL.

4. The method as claimed in claim 1, wherein the localization domain is KDEL.

5. A nucleic acid construct comprising a DNA sequence encoding a fusion protein, operably linked to a promoter for expression in a cell, wherein the fusion protein comprises
(a) a truncated soluble low density lipoprotein receptor, which includes the functional low density lipoprotein binding domain, but does not include the membrane binding domain or the domain associated with O-linked sugars, and
(b) a localization domain signal peptide, which retains the fusion protein in the endoplasmic reticulum of a cell.

6. The DNA construct as claimed in claim 5, wherein the low density lipoprotein receptor is LDL-$R^{354}$.

7. The DNA construct as claimed in claim 5, wherein the localization domain is selected from the group consisting of the amino acid sequences KDEL, KEEL, HDEL, DDEL, QDEL, ADEL and SDEL.

8. The DNA construct as claimed in claim 5, wherein the localization domain is KDEL.

9. A nucleic acid construct for the lowering of serum cholesterol levels in a mammal comprising a DNA sequence encoding a fusion protein, operably linked to a promoter for expression in a cell, wherein the fusion protein comprises (a) the truncated soluble low density lipoprotein receptor LDL-$R^{354}$, and (b) the localization domain signal peptide KDEL, which retains the fusion protein in the endoplasmic reticulum of a cell.

10. A nucleic acid construct for the lowering of serum cholesterol levels in a mammal comprising a DNA sequence encoding a fusion protein, operably linked to a promoter for expression in a cell, wherein the fusion protein comprises (a) the truncated soluble low density lipoprotein receptor LDL-$R^{354}$, and (b) the localization domain signal peptide, which retains the fusion protein in the endoplasmic reticulum of a cell, wherein the localization domain is selected from the group consisting of the amino acid sequences KDEL, KEEL, HDEL, DDEL, QDEL, ADEL and SDEL.

11. A method for the lowering of serum cholesterol levels in a mammal comprising the steps of:
preparing a nucleic acid construct comprising a DNA sequence encoding a fusion protein, operably linked to a promoter for expression in a cell, wherein the fusion protein comprises (a) the truncated soluble low density lipoprotein receptor LDL-$R^{354}$, and (b) the localization domain signal peptide KDEL, which retains the fusion protein in the endoplasmic reticulum of a cell; and
administering the nucleic acid construct systemically to the mammal, wherein expression and production of said fusion protein results in the lowering of serum cholesterol levels in said mammal.

12. A method for the lowering of serum cholesterol levels in a mammal comprising the steps of:
preparing a nucleic acid construct comprising a DNA sequence encoding a fusion protein, operably linked to a promoter for expression in a cell, wherein the fusion protein comprises (a) the truncated soluble low density lipoprotein receptor LDL-$R^{354}$, and (b) a localization domain signal peptide, which retains the fusion protein in the endoplasmic reticulum of a cell, wherein the localization domain is selected from the group consisting of the amino acid sequences KDEL, KEEL, HDEL, DDEL, QDEL, ADEL and SDEL; and administering the nucleic acid construct systemically to the mammal, wherein expression and production of said fusion protein results in the lowering of serum cholesterol levels in said mammal.

* * * * *

UNITED STATES PATENT AND TRADEMARK OFFICE
CERTIFICATE OF CORRECTION

PATENT NO. : 7,517,860 B1  Page 1 of 1
APPLICATION NO. : 09/620820
DATED : April 14, 2009
INVENTOR(S) : Alan D. Attie, Donald L. Gillian-Daniel and Paul W. Bates It is certified that error appears in the above-identified patent and that said Letters Patent is hereby corrected as shown below:

Column 1, line 46, the word "in" is missing from the phrase: "...secreted into the bloodstream. While the bloodstream, VLDL..." When corrected, line 46 should read: "...secreted into the bloodstream. While in the bloodstream, VLDL..."

Column 4, lines 29-30, the amino acid "glu" is missing from the phrase: "The amino acid sequence gln-lys-ala-val-lys-asp-leu-stop (QKAVKDELstop)..." When corrected, the phrase should read: "The amino acid sequence gln-lys-ala-val-lys-asp-glu-leu-stop (QKAVKDELstop)..."

Signed and Sealed this

Second Day of June, 2009

JOHN DOLL
*Acting Director of the United States Patent and Trademark Office*

SEQUENCE LISTING

```
<160> NUMBER OF SEQ ID NOS: 8

<210> SEQ ID NO 1
<211> LENGTH: 4
<212> TYPE: PRT
<213> ORGANISM: Unknown Organism
<220> FEATURE:
<223> OTHER INFORMATION: Description of Unknown Organism: vertebrates

<400> SEQUENCE: 1

Lys Asp Glu Leu
  1

<210> SEQ ID NO 2
```

-continued

```
<211> LENGTH: 4
<212> TYPE: PRT
<213> ORGANISM: Unknown Organism
<220> FEATURE:
<223> OTHER INFORMATION: Description of Unknown Organism: vertebrates

<400> SEQUENCE: 2

Lys Glu Glu Leu
  1

<210> SEQ ID NO 3
<211> LENGTH: 4
<212> TYPE: PRT
<213> ORGANISM: Saccharomyces cerevisiae

<400> SEQUENCE: 3

His Asp Glu Leu
  1

<210> SEQ ID NO 4
<211> LENGTH: 4
<212> TYPE: PRT
<213> ORGANISM: Kluyveromyces lactis

<400> SEQUENCE: 4

Asp Asp Glu Leu
  1

<210> SEQ ID NO 5
<211> LENGTH: 4
<212> TYPE: PRT
<213> ORGANISM: Kluyveromyces lactis

<400> SEQUENCE: 5

Gln Asp Glu Leu
  1

<210> SEQ ID NO 6
<211> LENGTH: 4
<212> TYPE: PRT
<213> ORGANISM: Schizosaccharomyces pombe

<400> SEQUENCE: 6

Ala Asp Glu Leu
  1

<210> SEQ ID NO 7
<211> LENGTH: 4
<212> TYPE: PRT
<213> ORGANISM: Plasmodium falciparum

<400> SEQUENCE: 7

Ser Asp Glu Leu
  1

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: construct

<400> SEQUENCE: 8

Gln Lys Ala Val Lys Asp Glu Leu
  1               5
```